US011100545B2

(12) United States Patent
Hummer

(10) Patent No.: US 11,100,545 B2
(45) Date of Patent: Aug. 24, 2021

(54) WEB-BASED HEALTH INDEX CALCULATOR

(71) Applicant: Gregory J. Hummer, Shaker Heights, OH (US)

(72) Inventor: Gregory J. Hummer, Shaker Heights, OH (US)

(*) Notice: Subject to any disclaimer, the term of this patent is extended or adjusted under 35 U.S.C. 154(b) by 89 days.

(21) Appl. No.: 13/895,727

(22) Filed: May 16, 2013

(65) Prior Publication Data
US 2013/0311197 A1 Nov. 21, 2013

Related U.S. Application Data

(60) Provisional application No. 61/648,180, filed on May 17, 2012.

(51) Int. Cl.
| | | |
|---|---|---|
| G06Q 30/02 | (2012.01) |
| G16H 50/30 | (2018.01) |
| G16H 10/20 | (2018.01) |
| G06Q 10/10 | (2012.01) |

(52) U.S. Cl.
CPC ......... *G06Q 30/0283* (2013.01); *G06Q 10/10* (2013.01); *G16H 10/20* (2018.01); *G16H 50/30* (2018.01)

(58) Field of Classification Search
None
See application file for complete search history.

(56) References Cited

U.S. PATENT DOCUMENTS

| | | | | |
|---|---|---|---|---|
| 8,639,604 | B1* | 1/2014 | Abrahamson | 705/36 R |
| 2003/0149596 | A1* | 8/2003 | Bost | 705/2 |
| 2005/0240438 | A1* | 10/2005 | Day | 705/2 |
| 2008/0010086 | A1* | 1/2008 | Skelly et al. | 705/4 |
| 2010/0173619 | A1* | 7/2010 | Hua et al. | 455/414.2 |
| 2010/0287076 | A1* | 11/2010 | Robinson | G06Q 30/06 705/31 |
| 2012/0191469 | A1* | 7/2012 | Akradi | 705/2 |

OTHER PUBLICATIONS

Financial Calculator, Quit Smoking Calculator, Nov. 27, 2011 <https://web.archive.org/web/20111127152351/http://www.financialcalculator.org/personal-finance/stop-smoking-calculator>.*

Baby2See, Quit it Now: Cigarette and Alcohol use cost Calculator, Aug. 15, 2011, <https://web.archive.org/web/20110815025459/http://www.baby2see.com/medical/cigarettes_alcohol.html>.*

* cited by examiner

*Primary Examiner* — Gregory Lultschik
*Assistant Examiner* — William G Lultschik
(74) *Attorney, Agent, or Firm* — Fay Sharpe LLP

(57) ABSTRACT

When calculating an individual's health index as a function of health index parameters including biometric parameters and behavioral parameters, a monetary cost is associated with each health index parameter, and the costs for all health index parameters are aggregated and displayed to a user via a graphical user interface. The user is then permitted to adjust one or more health index parameters, and the aggregate health cost is updated to show the user the amount of health cost savings that can be achieved by different health index parameter adjustments. In this manner, an individual is incentivized to improve his health in order to save money.

12 Claims, 13 Drawing Sheets

41

Health Savings Calculator

Please answer the following questions BEFORE you begin using the Health Index Calculator™.

1. Are you aware that you can improve your ability to accumulate wealth by changing your health habits?
    a. ☐ Yes
    b. ☐ No
2. Are you aware of the amount of money that is "locked up" in your current state of your health?
    a. ☐ Yes
    b. ☐ No
3. Do you know of your employer sponsored health and wellness resources that can help you maintain or improve your health?
    a. ☐ Yes
    b. ☐ No
4. I currently engage in my employer sponsored health and wellness resources in an effort to maintain or improve my health?
    a. ☐ Yes
    b. ☐ No
5. Do you know of your employer sponsored financial resources that can help you invest in your financial future?
    a. ☐ Yes
    b. ☐ No
6. I currently invest in my employer sponsored 401K Plan, Health Savings Account or other retirement program?
    a. ☐ Yes
    b. ☐ No
    c. ☐ My Employer does not offer a 401K Plan, Health Savings Account, or other retirement?

FIG. 5

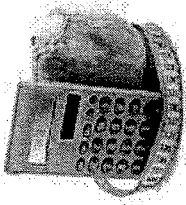
FIG. 6

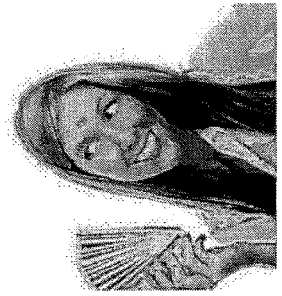
FIG. 8

Health Savings Calculator — 46

Thank your engagement in the Health Index Calculator. Now that you have used the calculator we would like to understand how your participation may have supported your health to wealth connection.
Please take a moment to answer the following questions:

1. The Health Index Calculator (HIC) improved my awareness/knowledge about how changes in my health habits can help me accumulate wealth.
    a. ○ Yes
    b. ○ No 2. The HIC helped me understand the amount of money that is "locked up" in my health and how I can transform good health into wealth.
    a. ○ Yes
    b. ○ No 3. The HIC raised my awareness about my employer sponsored health and wellness resources that can help me maintain or improve my health.
    a. ○ Yes
    b. ○ No 4. The HIC raised my awareness about my employer sponsored financial resources that can help me invest in my financial future.
    a. ○ Yes
    b. ○ No 5. The HIC provided me with the knowledge I need to understand how to turn my health in wealth and how to save for retirement.
    a. ○ Yes
    b. ○ No
    c. ○ Not Sure 6. As a result of the HIC, I was able to access an investment advisor to help me with my financial planning.
    a. ○ Yes
    b. ○ No 7. As a result of the HIC, I have a better outlook for my financial future and my ability to accumulate wealth.
    a. ○ Yes
    b. ○ No 8. As a result of the HIC, I plan to change my health habits in the next three (3) to six (6) months.
    a. ○ Yes
    b. ○ No 9. The Health Index Calculator was easy to use?
    a. ○ Yes
    b. ○ No

[Submit] — 1102

FIG. 11

WEB-BASED HEALTH INDEX CALCULATOR

The present application claims the benefit of U.S. Provisional Application No. 61/648,180, filed May 17, 2012, which is incorporated herein by reference in its entirety.

BACKGROUND

The subject application relates to a web-based health index calculator that facilitates incentivizing a user to improve his health in order to realize monetary savings.

Studies suggest that 80% of all preventable chronic disease and 70% of preventable healthcare costs are attributable to small number of health-related conditions and behaviors. Conventional approaches to calculating costs associated with particular behaviors do not account for cost savings attributable to improvements to such behaviors. Similarly, conventional systems for calculating retirement savings do not account for lost savings that are attributable to poor health behavior and poor health in general.

Moreover, traditional approaches to educating consumers about healthcare-related costs and/or financial issues do not provide information related to promoting fiscal savings as a function of improved health, tax savings related thereto under current tax laws that permit tax-free investment growth of healthcare-related savings accounts, FICA savings for employers, etc. Additionally, conventional systems do not permit users to visualize health-related goals and the fiscal rewards associated with achieving said goals.

Accordingly, there is an unmet need for systems and/or methods that facilitate overcoming the aforementioned deficiencies.

BRIEF DESCRIPTION

According to one aspect, system that facilitates calculating a monetary cost associated with an individual's health index comprises a processor that executes computer-executable instructions for calculating a user's health index and a monetary cost associated therewith, a computer-readable medium that stores the computer-executable instructions, and a server comprising the processor and the computer-readable medium and configured to provide Internet access to the processor for presenting calculated cost information to the user via a graphical user interface on a user device. The instructions comprise receiving a plurality of health index parameter values, calculating a cost associated with each health index parameter, aggregating the costs associated with respective health index parameters, and providing the aggregate cost to the user. The instructions further comprise receiving input related to an adjustment to at least one health index parameter value, updating the cost associated with the adjusted health index parameter and updating the aggregate cost, and providing the updated aggregate cost to the user.

According to another aspect, a method of calculating a monetary cost associated with an individual's health index, comprising receiving a plurality of health index parameter values, calculating a cost associated with each health index parameter, aggregating the costs associated with respective health index parameters, and providing the aggregate cost to the user. The method further comprises receiving input related to an adjustment to at least one health index parameter value, updating the cost associated with the adjusted health index parameter and updating the aggregate cost, and providing the updated aggregate cost to the user.

According to another aspect, a graphical user interface presented to a user on a user device comprises a health index calculator that receives user-specified health index parameter values for a plurality of health index parameters, a selectable icon for each of the plurality of health index parameters, and an adjustable icon associated with each of the selectable icons and via which one or more health index parameter values are adjustable. The interface further comprises a personal information panel in which user information is presented, a financial analysis panel in which financial information associated with the plurality of health index parameters is presented, and a selectable recalculation icon that, when selected by the user, causes the financial information to be recalculated as a function of one or more adjusted health index parameter values.

BRIEF DESCRIPTION OF THE DRAWINGS

FIG. 5 shows a screenshot of a preliminary survey, which can be presented to a user when the user initially logs in to the calculator or registers for a member account.

FIG. 6 shows a screenshot of a graphical representation of a health index calculator webpage, via which the user interfaces with the calculator and which comprises a plurality of fields that are populated by user.

FIG. 8 shows a screenshot of the results page and which user has adjusted the slider bars associated with each health index parameter that the user desires to improve.

FIG. 11 is a screenshot of a post-calculation survey that is presented to the user on the user's device in order to prompt the user to provide feedback regarding the user's experience with the calculator.

DETAILED DESCRIPTION

In accordance with various features described herein, systems and methods are described that facilitate providing a graphical health index calculator for or an individual (e.g., employees and their family members, insurance customers and their family members, etc.) via a web based cloud application that depicts a dollar amount that one or more bad health behaviors cost an individual per unit of time (e.g., per week, per month, etc.). In other embodiments, the application is a mobile application or "app." As used herein, "algorithm" or "module" refers to a set of computer-executable instructions stored on a computer-readable medium and executable by a processor or other computing device, as will be appreciated by those of skill in the art.

Figure 1:
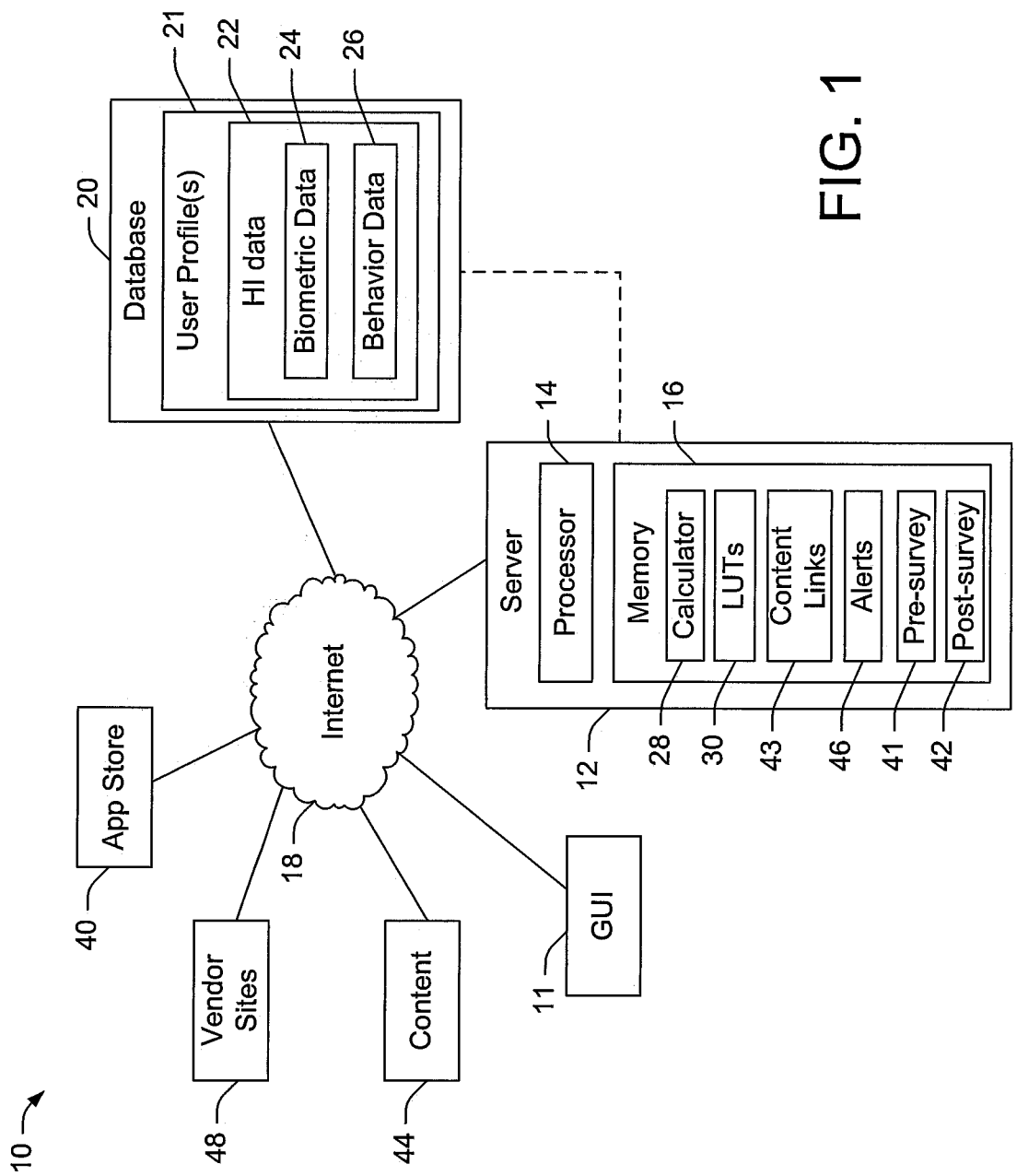
FIG. 1 illustrates a system that facilitates providing the herein-described health index calculator, e.g., via a graphical user interface (GUI).

With reference to FIG. 1, a system 10 is illustrated that facilitates providing the herein-described health index calculator, e.g., via a graphical user interface (GUI) 11. The system 10 includes a server 12 with a processor 14 that executes, and a memory 16 that stores, computer-executable instructions for performing the various functions, methods, techniques, algorithms, etc., described herein. The server is coupled to the Internet 18, by which it communicates with, accesses, etc., the GUI 11 (e.g., a personal computer, laptop, tablet, smartphone, etc.). Additionally, the server can access a database 20 that stores user profiles 21 comprising health index parameter information 22. The health index parameter information includes biometric data 24 (e.g., blood pressure or other vital sign readings, weight measurements, body mass index, and/or any other biometric data suitable for calculating all or part of a user's health index) and health behavior data 26 (e.g., number of packs of cigarettes smoked per day, alcoholic drinks consumed per day, etc.). For instance, biometric data may be entered by the user (e.g., selected from a pop-up or drop-down menu, entered as text in a specified field, etc.), and/or provided by the user's employer (e.g., having been collected as part of a wellness program, etc.) The health index parameter data 22 may be entered by the user (e.g., via the GUI) or may be medical record data that the user has authorized to be made available to a provider of the health index calculator. Although depicted as being stored in a database 20 coupled to the GUI and server via the internet, the user profile can reside on the user's GUI 11 or at any other suitable location (e.g., the server 12, a remote server or computer-readable storage device, etc.). In another embodiment, the database 20 is a distributed database and/or the server 12 is a distributed server. In another embodiment, the server 12 and database 20 are directly coupled to each other.

The user's health index data 22 is uploaded to, or retrieved by, the server 18 and loaded into a calculator module 28 stored in memory 16. Biometric data can include, but is not limited to: BMI, height, weight, blood pressure (systolic and diastolic), cholesterol (high density lipoprotein, low density lipoprotein, a ratio of HDL to LDL, etc.), blood glucose levels, triglyceride levels, and/or any other suitable biometric data that can be compared to respective baseline or threshold values to estimate or calculate a dollar cost for a behavior associated with respective biometric parameters. Other health factors evaluated by the calculator can include user-entered health behavior information 26 such as a number of alcoholic drinks consumed per day, average cost per drink, a number of packs of cigarettes smoked per day, average cost of the individual's pack of cigarettes, stress level information, exercise activity levels, etc.

The calculator calculates an actual monetary cost associated each parameter described by the health index data (e.g., using user-entered values and/or predetermined values stored in one or more lookup tables (LUT) 30. For instance, a user who smokes two packs of cigarettes a day and has a body mass index (BMI) indicative of mild obesity (e.g., over 30) can be presented with a dollar value for the two packs of cigarettes, which may be adjustable as a function of current market prices, geographic location or zip code, user-entered price information, etc., as well as a dollar value describing the cost of being mildly obese, which may be calculated as a function of, for instance, increased food costs, reduced energy levels, decreased productivity, or some other suitable and/or predetermined factor(s) or algorithm. Additionally, the user can be presented, via the GUI, with an aggregate or total dollar amount representing the sum of the individual costs of each biometric parameter and/or behavior. The calculator can, according to various examples: calculate the additional cost of food per month using the BMI of an overweight user (e.g., via a lookup table or the like); calculate a number of "lost days" from work for certain behaviors and dollar amounts corresponding thereto; calculate "lost productivity" in terms of dollars; calculate the direct medical cost to the employer for individual bad health behaviors; etc.

In one example, the GUI provides a manually adjustable graphical slider bar 26 (e.g., via a slider-type hypertext mark-up language (HTML) design, or any other manually adjustable graphical tool or icon) to allow the user to adjust the bad health behavior parameters and/or biometric parameters to see the change in cash cost. For instance, the user can adjust the number of packs of cigarettes consumed per day to see the savings he will achieve in the selected unit of time (e.g., a month, a year, etc.).

In another example, the user can adjust the total cost of his bad behaviors, e.g., to save for example $200 a month. The user also selects one or more individual biometric parameters representing respective behaviors. For instance, the user may select packs of cigarettes consumed per day, and the calculator will indicate to the user an updated number of packs of cigarettes per day to which the user should limit himself in order to reduce the overall cost of his bad health behaviors by $200 per month. Alternatively, the user may select BMI as the biometric parameter to be adjusted in order to save the $200. The calculator executes an algorithm that outputs to the user a target BMI that will achieve the desired savings (e.g., through decreased food costs, increased productivity, or any other suitable factors as calculated by the algorithm). In yet another example, the user adjusts a slider bar 26 for one or more of the health index parameters to view the effect of such adjustment(s) on the individual and aggregate monthly costs associated with the bad behavior(s).

According to another example, the user selects or inputs an interest rate and the calculator displays savings amounts attributable to improved health behavior over a selected period of time (e.g., months, years, a planned retirement date, etc.). For instance, if the user in the foregoing example quits smoking and invests the savings at the selected interest rate, the calculator outputs a total savings, with interest, that will be achieved over a time period selected or input by the user. The calculator can also be employed by financial planners to find additional income for their clients to retire on, as well as by healthcare and/or insurance providers as a tool to drive health behavior change in order to decrease health care cost and produce a more healthy employee or insured.

In another embodiment, the user's health plan deductible and/or co-pay amount is input to the calculator, which estimates an actual out of pocket healthcare cost associated with any and all of the bad health behaviors.

As previously mentioned, the system 10 comprises the processor 14 that executes, and memory 16 that stores, computer-executable instructions and/or computer-readable data (e.g., a software package or product) for performing the various techniques and/or methods described herein. The memory 16 may be a computer-readable recording medium on which a control program or software product is recorded, such as a disk, hard drive, or the like. Common forms of computer-readable media include, for example, floppy disks, flexible disks, hard disks, magnetic tape, or any other magnetic storage medium, CD-ROM, DVD, or any other optical medium, a ROM, a PROM, an EPROM, a FLASH-EPROM, or other memory chip or cartridge, or any other tangible medium from which a computer can read and use. Alternatively, the methods may be implemented in a transmittable carrier wave in which the control program is embodied as a data signal using transmission media, such as acoustic or light waves, such as those generated during radio wave and infrared data communications, and the like.

According to another feature, an application store or other digital distribution platform (e.g., iTunes, Google Play, the Windows Store, or the like) can be accessed by the user via the GUI (e.g., a personal computer, tablet, laptop, smart phone, mobile device, or the like) to download a health index calculator application ("app") via which the user interfaces with the calculator 28. The web-based application and/or the mobile "app" can retrieve the user's biometric data from an employer's wellness program data source and/or receive biometric data via user input into the health index calculator.

Regardless of whether a user is using the app version or the web-based version of the calculator 28, the user is prompted by the processor 14 to fill out a preliminary survey 41 comprising questions related to the user's understanding of the connection between health and finances. When the user is done using the calculator, the server can present to the user a final survey 42 that comprises questions related to the user's experience with the calculator 28.

User responses to the survey questions and/or user-entered health index parameter data can be used, e.g., to tailor content delivery to the user, via the GUI. For instance, the server can send emails, text messages, or other alerts to the GUI to remind the user to stay on target with regard to the user's stated health goals. Additionally, links 43 to relevant content can be transmitted to the GUI and presented to the user (e.g., as hyperlinks, icons, or in any other suitable, user-selectable manner), and upon selection thereof by the user, the user's device is redirected to content 44 at a webpage corresponding to the selected link. Content 44 may include health-related articles, studies, products, or other content relevant to the user's stated goals.

Additionally, alerts 46 (and their respective icons or graphical representations) and/or other content can be stored in the server memory 16 and directly transmitted to the user's device (e.g., as email attachments or the like). For instance, email or text alerts can be generated and stored, matched to a particular user as a function of the user's stated health goals (e.g., by comparing the users stated goals, entered health parameter information, etc., to metadata associated with the respective content and/or alert(s)), and matched alerts can be delivered to the user.

Content and/or alert delivery can also be tied to a particular time of day, such as a time of day when the user is likely to perform or omit an action related to the user's specified goals. For instance, a user who has indicated weight loss as a goal may receive alerts or reminders between meals, such as a reminder not to snack between meals and/or to walk 2 miles after work. In another example, a user who has indicated alcohol consumption reduction or cessation as a health behavior goal can receive a reminder at 5 pm that he can save money by not drinking alcohol that evening. In another example, a user who has indicated weight loss, blood pressure reduction, cholesterol reduction, and/or increased physical activity as health goals can receive a reminder in the late afternoon or evening inquiring whether the user has reached his daily goal of walking, e.g., 10,000 steps that day, or some other predetermined target activity level. The foregoing examples are presented by way of illustration and are not intended to limit the scope of the types of alerts or reminders and/or the times of day at which they are presented to the user, as will be understood by those skilled in the art. In another example the user can specify times of day and/or temporal intervals (e.g., every 3 hours, etc.) at which the alerts are transmitted to the user's device.

Content links 43 can also be presented to the user (e.g., via email, text, in conjunction with the health index calculator 28, or by any suitable means, etc.) that, when selected by the user, direct the user's device to respective vendors' sites 48. For instance, when a user indicates that smoking cessation and increased physical activity are among the user's goals, the links (or icons, etc.) can direct the user's device to, e.g., a website for a smoking cessation product and a website for a discount on athletic shoes, respectively. In other examples, the content links include business-to-business (B2B) marketing advertisements.

In another embodiment, the calculator application is "skinned" or otherwise adapted according to a particular corporate client's (i.e., an employer offering a wellness program to its employees that employees the herein-described health calculator) specifications. In this example, the calculator interface (see, e.g., FIGS. 5-11 and 13) is customized for each of a plurality of employers that subscribe to a service that provides the wellness program and/or the described health index calculator. For instance, health index parameters, icons representing the parameters, alert content (e.g., icons, content links, etc.), logos, can be configured specifically for each employer, which permits employers to have their specific wellness program content and objectives incorporated into the graphical interface.

Figure 2:
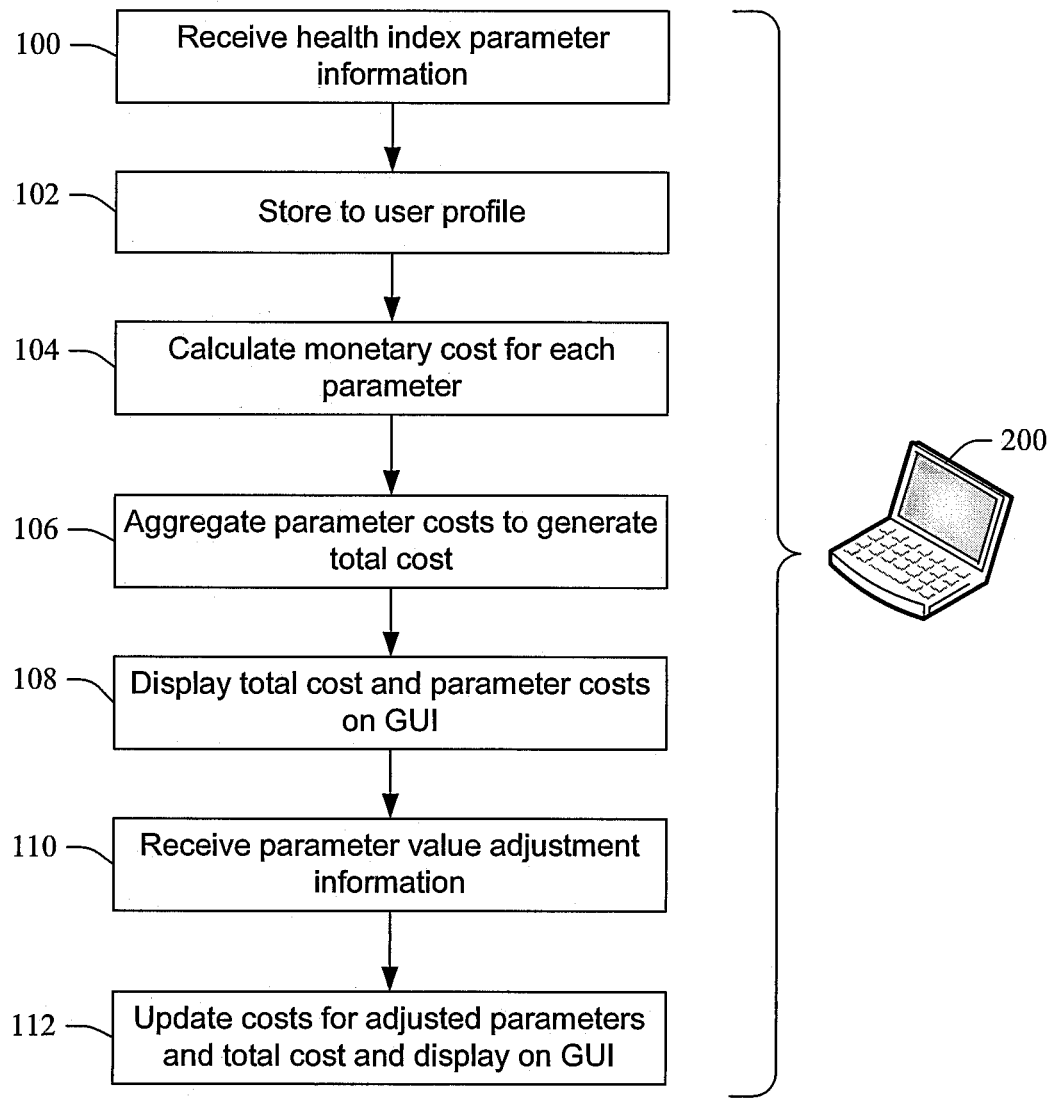
FIG. 2 illustrates a method for providing a user with a graphical representation of the user's health index with adjustable parameters, as well as a health index cost calculator, in accordance with various aspects described herein.

FIG. 2 illustrates a method related to calculating a monetary cost associated with a user's health index and presenting the user with a graphical representation thereof including adjustable parameters that the user can manipulate to see a cost savings associated with health behavior adjustments, in accordance with various features. While the method is described as a series of acts, it will be understood that not all acts may be required to achieve the described goals and/or outcomes, and that some acts may, in accordance with certain aspects, be performed in an order different that the specific orders described. The method of FIG. 2 may be implemented on a computer 200, as described below. Additionally, it will be appreciated that the method of FIG. 2 may be performed separately or in conjunction with each other.

FIG. 2 illustrates a method for providing a user with a graphical representation of the user's health index with adjustable parameters, as well as a health index cost calculator, in accordance with various aspects described herein. At 100, behavioral parameters (e.g., a number of packs of cigarettes smoke per day, etc.) and biometric parameter information (e.g., height and weight for BMI calculation, blood pressure and/or other vital sign measurement data, cholesterol level information, etc.) is received or retrieved. The information is stored in a user profile for the user on a computer-readable medium, at 102. At 104, calculator algorithm is executed to calculate a cost (e.g., a dollar amount or some other currency amount) associated with each of the adjustable health index parameters (e.g., biometric parameter data and user-entered behavior parameters). At 106, the costs calculated for each parameter are aggregated. At 108, the aggregate or total cost associated with the user's health index is output to the user on a display or GUI, along with individual parameter costs associated with each health index parameter. At 110, user input related to an adjustment of at least one of the health index parameters is received. At 112, updated dollar costs are output to the user for the adjusted health index parameter and the aggregated dollar cost is updated and presented to the user. Dollar cost updates are presented to the user in real time upon user adjustment of one or more health index parameters. In this manner, the user is permitted to adjust one or more health index parameters to see what the cost savings will be if the user adjusts his health behavior (e.g., by losing weight and reducing BMI, quitting smoking, etc.). The method thus provides a visual tool via which a user is encouraged to improve his health, thereby improving his work performance and reducing his and/or his employer's healthcare costs.

The method illustrated in FIG. 2 may be implemented in a computer program product that may be executed on a computer 200 or processor such as the processor 14 in the system of FIG. 1. Further, it is to be appreciated that any suitable computing environment can be employed in accordance with the present embodiments. For example, computing architectures including, but not limited to, stand alone, multiprocessor, distributed, client/server, minicomputer, mainframe, supercomputer, digital and analog can be employed in accordance with the present embodiments.

The computer can include a processing unit such as the processor 16 of FIG. 1, a system memory such as the memory 16 of FIG. 1, and a system bus that couples various system components including the system memory to the processing unit. The processing unit can be any of various commercially available processors (e.g., a central processing unit, a graphical processing unit, etc.). Dual microprocessors and other multi-processor architectures also can be used as the processing unit.

The system bus can be any of several types of bus structure including a memory bus or memory controller, a peripheral bus, and a local bus using any of a variety of commercially available bus architectures. The computer memory includes read only memory (ROM) and random access memory (RAM). A basic input/output system (BIOS), containing the basic routines that help to transfer information between elements within the computer, such as during start-up, is stored in ROM.

The computer can further include a hard disk drive, a magnetic disk drive, e.g., to read from or write to a removable disk, and an optical disk drive, e.g., for reading a CD-ROM disk or to read from or write to other optical media. The computer typically includes at least some form of computer readable media. Computer readable media can be any available media that can be accessed by the computer. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other magnetic storage devices, or any other medium which can be used to store the desired information and which can be accessed by the computer.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above can also be included within the scope of computer readable media.

A number of program modules may be stored in the drives and RAM, including an operating system, one or more application programs, other program modules, and program non-interrupt data. The operating system in the computer can be any of a number of commercially available operating systems.

A user may enter commands and information into the computer through a keyboard (not shown) and a pointing device or stylus (not shown), such as a mouse. Other input devices (not shown) may include a microphone, an IR remote control, a joystick, a game pad, a satellite dish, a scanner, or the like. These and other input devices are often connected to the processing unit through a serial port interface (not shown) that is coupled to the system bus, but may be connected by other interfaces, such as a parallel port, a game port, a universal serial bus (USB), an IR interface, etc.

A monitor (not shown), or other type of display device, may also be connected to the system bus via an interface, such as a video adapter (not shown). In addition to the monitor, a computer typically includes other peripheral output devices (not shown), such as speakers, printers etc. The monitor can be employed with the computer to present data that is electronically received from one or more disparate sources. For example, the monitor can be an LCD, plasma, CRT, etc. type that presents data electronically. Alternatively or in addition, the monitor can display received data in a hard copy format such as a printer, facsimile, plotter etc. The monitor can present data in any color and can receive data from the computer via any wireless or hard wire protocol and/or standard.

The computer can operate in a networked environment using logical and/or physical connections to one or more remote computers, such as a remote computer(s). The remote computer(s) can be a workstation, a server computer, a router, a personal computer, microprocessor based entertainment appliance, a peer device or other common network node, and typically includes many or all of the elements described relative to the computer. The logical connections depicted include a local area network (LAN) and a wide area network (WAN). Such networking environments are commonplace in offices, enterprise-wide computer networks, intranets and the Internet.

When used in a LAN networking environment, the computer is connected to the local network through a network interface or adapter. When used in a WAN networking environment, the computer typically includes a modem, or is connected to a communications server on the LAN, or has other means for establishing communications over the WAN, such as the Internet. In a networked environment, program modules depicted relative to the computer, or portions thereof, may be stored in the remote memory storage device. It will be appreciated that network connections described herein are exemplary and other means of establishing a communications link between the computers may be used.

Figure 3:
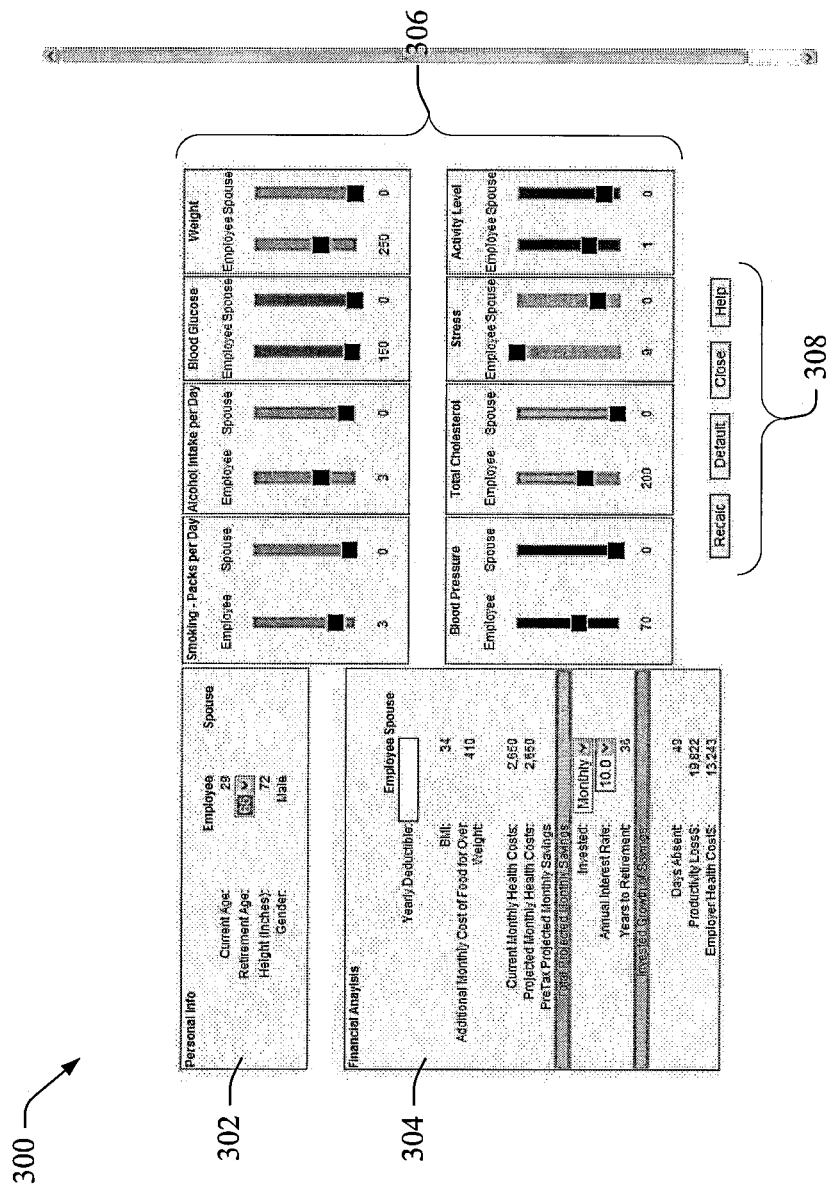
FIG. 3 illustrates a screenshot of a graphical representation of the health index calculator that is presented to a user prior to user adjustment, in accordance with various aspects set forth herein.

FIG. 3 illustrates a screenshot of a graphical representation 300 of the health index calculator that is presented to a user prior to user adjustment, in accordance with various aspects set forth herein. The calculator includes a personal information field 302 that in which information is entered and/or presented including but not limited to an employee's or insured's current age, retirement age, height, and gender. The user may be the employee or insured party or may be the employee's employer or another party. The calculator further includes a financial analysis field in which information is entered and/or presented including but not limited to the employee's yearly deductible for health insurance, the employee's BMI, additional food cost associated therewith, current and projected monthly health care costs, projected savings, investment information related to investment growth of the projected savings, productivity loss and costs thereof as a function of the employee's health index, etc.

Also graphically presented to the user is a plurality of adjustable health index parameter fields, including but not limited to a "packs smoked per day" field, an alcohol intake field, a blood glucose field, a weight field, a blood pressure field, a cholesterol field, a stress level field, and an activity level field. Also provided are a plurality of user-selectable icons or buttons 308, including buttons for recalculating the user's healthcare index and cost thereof, for resetting the fields to default levels, for closing the application, and for opening a help menu.

As can be seen in FIG. 3, the present employee smokes three packs of cigarettes a day, has three alcoholic drinks per day, weight 250 pounds and has a BMI of 34, and has a stress level of 9 and an activity level of 1. These negative behaviors and biometric parameter values contribute to a monthly health cost of $2650, productivity loss of almost $20,000 a year, and employer health costs of $13,243.

Figure 4:
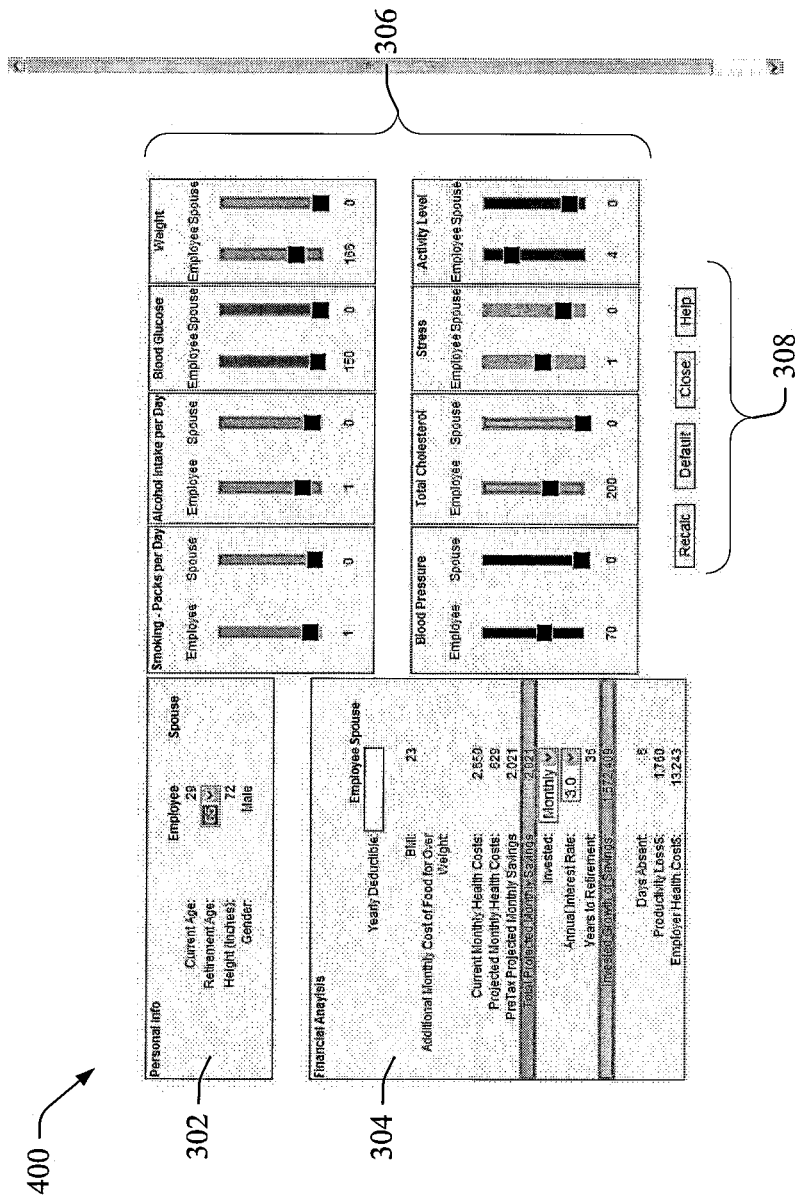
FIG. 4 illustrates a screenshot of a graphical representation of the health index calculator that is presented to a user after user adjustment, in accordance with various aspects set forth herein.

FIG. 4 illustrates a screenshot of a graphical representation 400 of the health index calculator that is presented to a user after user adjustment, in accordance with various aspects set forth herein. As can be seen, several health index parameters have been adjusted, including the number of packs smoked per day (reduced to 1 from 3), the number of alcoholic drinks per day (reduced to 1 from 3), weight (reduced to 166 from 250, for a corresponding reduction in BMI to 23 from 34), stress (reduced to 1 from 9) and activity level (increased from 1 to 4). As a result, the employee can save $2021 per month on health costs, and the reduction in productivity loss attributable to health index is reduced by approximately $18,000 per year.

In this manner, the employee can manipulate different parameter fields 308 and visualize a monetary reward in the form of health cost savings for improving his health and habits. Additionally or alternatively, an employer can manipulate different fields to calculate savings associated with improved worker productivity, reduced sick days, etc., as a function of employee health index. The Employer, for example, can initiate measures to reduce employee stress, encourage exercise and/or smoking cessation, etc.

FIG. 5 shows a screenshot of a preliminary survey 41, which can be presented to a user when the user initially logs in to the calculator or registers for a member account. The survey comprises a plurality of questions that can be used to assist in generating and/or presenting a graphical representation of the health index calculator to the user. The questions presented in survey example of FIG. 5 are provided by way of illustration only and are not intended to limit the scope of the questions that may be asked in the preliminary survey, as will be appreciated by one of skill in the art.

FIG. 6 shows a screenshot of a graphical representation of a health index calculator webpage 600, via which the user interfaces with a graphical interface 601 of the calculator 28 (see, e.g., FIG. 1) and which comprises a plurality of fields that are populated by user. For example, the user enters his name into first and last name fields, and specifies his age or birth date, gender and height. Additionally the calculator interface 601 includes a plurality of entry fields corresponding to each of a plurality of health parameters including but not limited to, user weight, packs of cigarettes smoked per day and price thereof, number of alcoholic beverages consumed per day and price thereof, glucose level, cholesterol level, diastolic blood pressure, activity level, and stress level. Finally, the calculator interface 601 includes fields wherein the user enters his daily income and an e-mail address (and/or phone number, e.g. to receive text messages). Additionally, associated with each of the health parameters is a corresponding icon, including a weight icon 602, a smoking icon 604, an alcoholic drink icon 606, a glucose level icon 608, a cholesterol level icon 610, a blood pressure icon 612, an activity level icon 614, and a stress level icon 616, which are selectable by the user to view additional information associated with each respective health parameter. A financial planner icon 618 is also provided, which the user can select to be redirected to a financial planning website (e.g. a bank or other financial plan provider). It will be appreciated that although the herein-presented systems and methods are described with regard to eight health index parameters, more or fewer parameters may be employed in conjunction there with, and that the herein described systems and methods are not limited to using eight health index parameters, as will be appreciated by one of skill in the art.

In the example illustrated in the screenshot of FIG. 6, the user is a male born in 1960, who is 5'9" tall and weighs 211 pounds. The user has indicated that he smokes 0.5 packs of cigarettes per day cost of $7.50 per pack and consumes 1.5 drinks per day at a cost $6 per drink. The user has further indicated that he has a normal glucose level, a high cholesterol level, a high diastolic blood pressure, a low physical activity level, and high stress level. Additionally, the user has indicated that he makes $180 per day. Once the user has populated the fields in the calculator interface 601, he clicks on or otherwise selects a "calculate" icon 620, upon which his information is transmitted to the server (see, e.g., FIG. 1) which performs the herein described calculations and returns the calculated results to the user's device.

Figure 7:
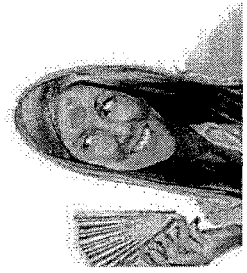
FIG. 7 shows a screenshot of a results page that is presented to a user via a graphical user interface on the user's device, in accordance with one or more aspects described herein.

FIG. 7 shows a screenshot of a results page 700 that is presented to a user via a graphical user interface on the user's device, in accordance with one or more aspects described herein. The results page 700 includes a personal information panel 702 in which is presented user information including but not limited to the user's name, current age, anticipated retirement age (which may be adjusted by the user), height, and gender. The results page also includes a financial analysis panel 704 in which the user enters his yearly deductible and copayment information. Calculated results presented to the user include his body mass index (BMI), an estimated additional monthly cost for food required to maintain his BMI, current and projected monthly health behavior costs, pretax monthly savings, and total projected monthly savings. Additionally, the financial analysis panel 704 includes calculated invested growth savings associated with health behavior changes and tax savings due to health behavior changes, which are a function of the number of years left until the user retires and investment parameters selected by the user (e.g. investment frequency, annual interest rate, tax rate, etc.). Also present in the financial analysis panel 704 are an estimated number of workdays missed due to poor health behavior and/or biometrics, a dollar amount associated with productivity loss, and insurance/employer health costs associated with the user's poor health behavior and/or biometrics.

In the illustrated example, the user's poor health behavior causes him to have a mildly obese BMI of 31, which is estimated to cost him $273 per month in additional food costs to maintain. The aggregate behavior cost for all of his poor health behaviors is calculated to be $1429 per month.

The results page also includes each of the health parameter icons (e.g. smoking, drinking, glucose, weight, blood pressure, cholesterol, stress, physical activity, etc.) described with regard to FIG. 6. Associated with each health parameter icon is a slider bar 705 on which a slider is positioned at the user's current level (as input into the calculator interface of FIG. 6 by the user). The user can adjust one or more health parameter slider bars 705 to a target level or goal, and the magnitude of the change of the health index parameter value is presented to the user in real time based on the change in the position of the slider. Once the user has set his goals using the slider bars (or any other suitable adjustment means), the user selects a "recalculate" icon 706, upon which information associated with the user's goals is transmitted to the server, which returns recalculated financial analysis information. If the user desires, the user can select a "reset" icon 708 to reset the slider bars to his "current" levels as they were input into the calculator (see, e.g., FIG. 6). Additionally the user is provided with a "frequently asked questions" (FAQ) icon 710, which the user may select to access additional information.

FIG. 8 shows a screenshot of an adjusted results page 800 wherein the user has adjusted the slider bars 705 associated with each health index parameter that the user wants to improve. For example, the user has set a goal to quit smoking (i.e., reduce the number of packs per day from 0.5 to 0), and to lose 30 pounds. The user has also set goals to reduce his blood pressure from high to normal, to reduce his cholesterol from high to normal, to reduce his stress from high to medium, and to increase his physical activity level from low to medium. After setting his goals, the user has selected (e.g., clicked on) the recalculation icon 706 in order to update the financial analysis panel 704. As can be seen in the illustrated example, if the user achieves his goals, his BMI will be reduced to 27 and the additional monthly cost for food to maintain his BMI will be reduced to $91 per month. Additionally, the user will save $854 in pretax dollars each month by adjusting his behavior to meet his goals. If the user invests the $854 each month until retirement at 3% annual interest and a tax rate of 32%, the user's invested growth of the money saved (i.e. the value at retirement) will be $148,174, and the user will enjoy a tax savings of $47,415.

Figure 9:
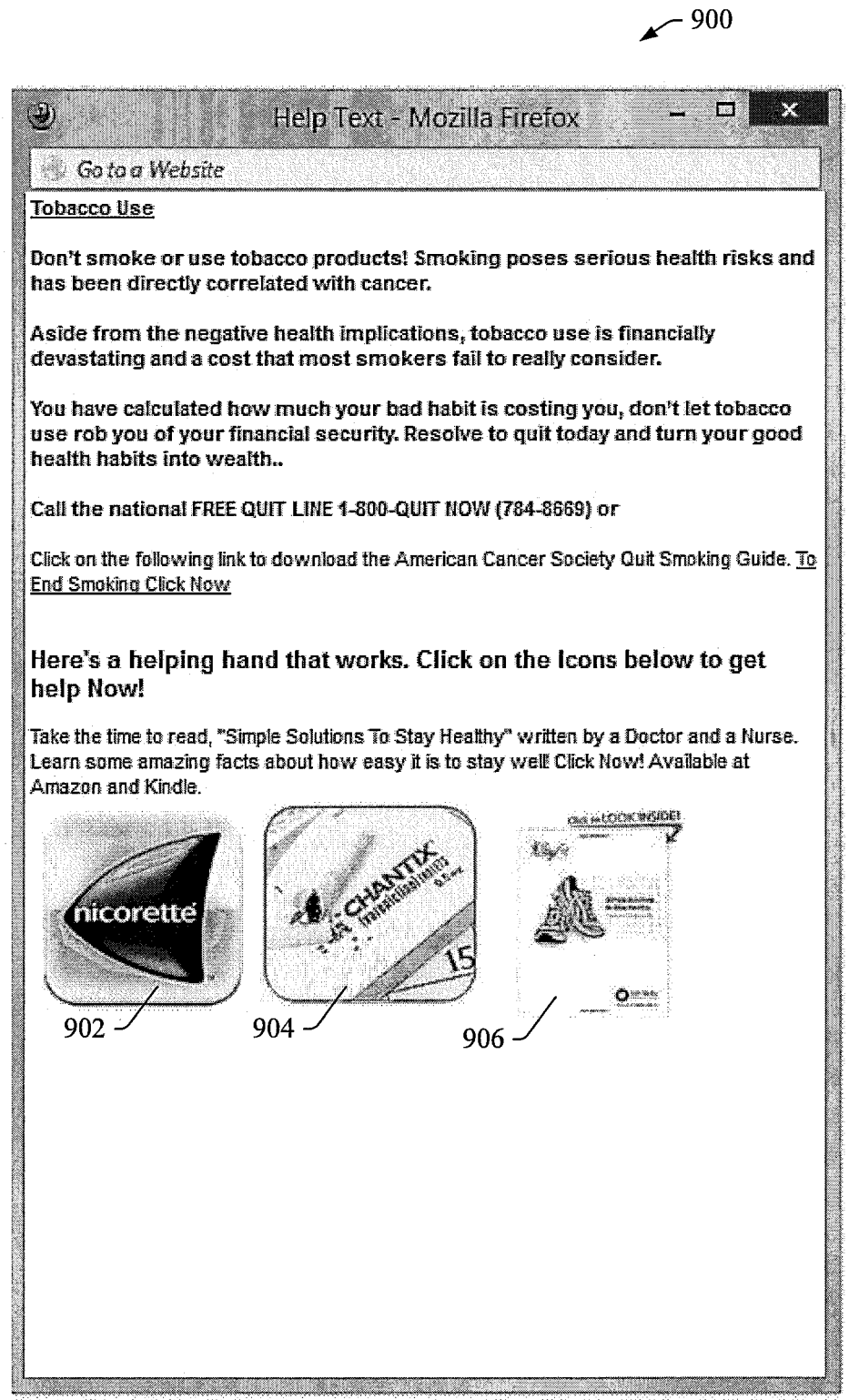
FIG. 9 shows a screenshot of a webpage that is presented to the user when the user selects or clicks on the smoking icon in any of the above-described webpages to view additional information related to tobacco use.

FIG. 9 shows a screenshot of a webpage 900 that is presented to the user when the selects or clicks on the smoking icon 604 in any of the above-described calculator interface screenshots to view additional information related to tobacco use. Presented in the webpage, in addition to the supplemental information, are icons 902, 904 representing links to third-party vendors' sites for products relating to smoking cessation, and an icon 906 that represents a link to third-party vendor site for product (e.g., a book) for improving personal health.

Figure 10:
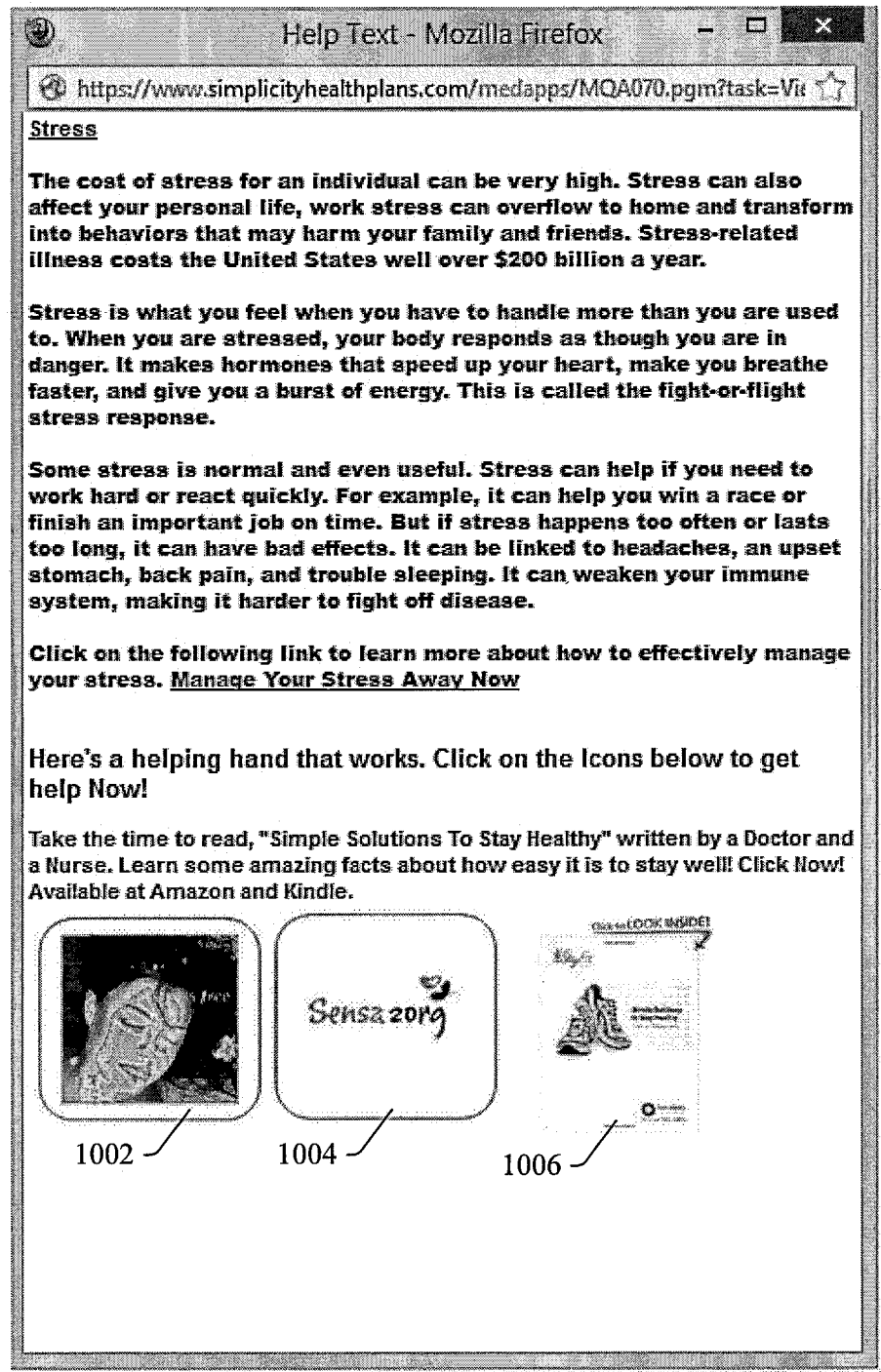
FIG. 10 shows a screenshot of a webpage that is presented to the user upon selecting the stress icon on any of the above-described webpages to view additional information related to stress reduction.

FIG. 10 shows a screenshot of a webpage 1000 that is presented to the user upon selecting the stress icon 616 on any of the above-described webpages to view additional information related to stress reduction. Presented in the webpage, in addition to the supplemental information, are icons 1002, 1004 representing links to third-party vendors' sites for products relating to stress reduction, and an icon 1006 that represents a link to third-party vendor site for product (e.g., a book) for improving personal health.

FIG. 11 is a screenshot of a post-calculation survey 46 that is presented to the user on the user's device in order to prompt the user to provide feedback regarding the user's experience with the calculator. Once the user has indicated an answer to each of the survey questions, the user selects a "submit" icon 1102 to submit the survey, which is stored at the server (FIG. 1). The user's feedback can then be used to refine the calculator, presentation thereof, etc.)

Figure 12:
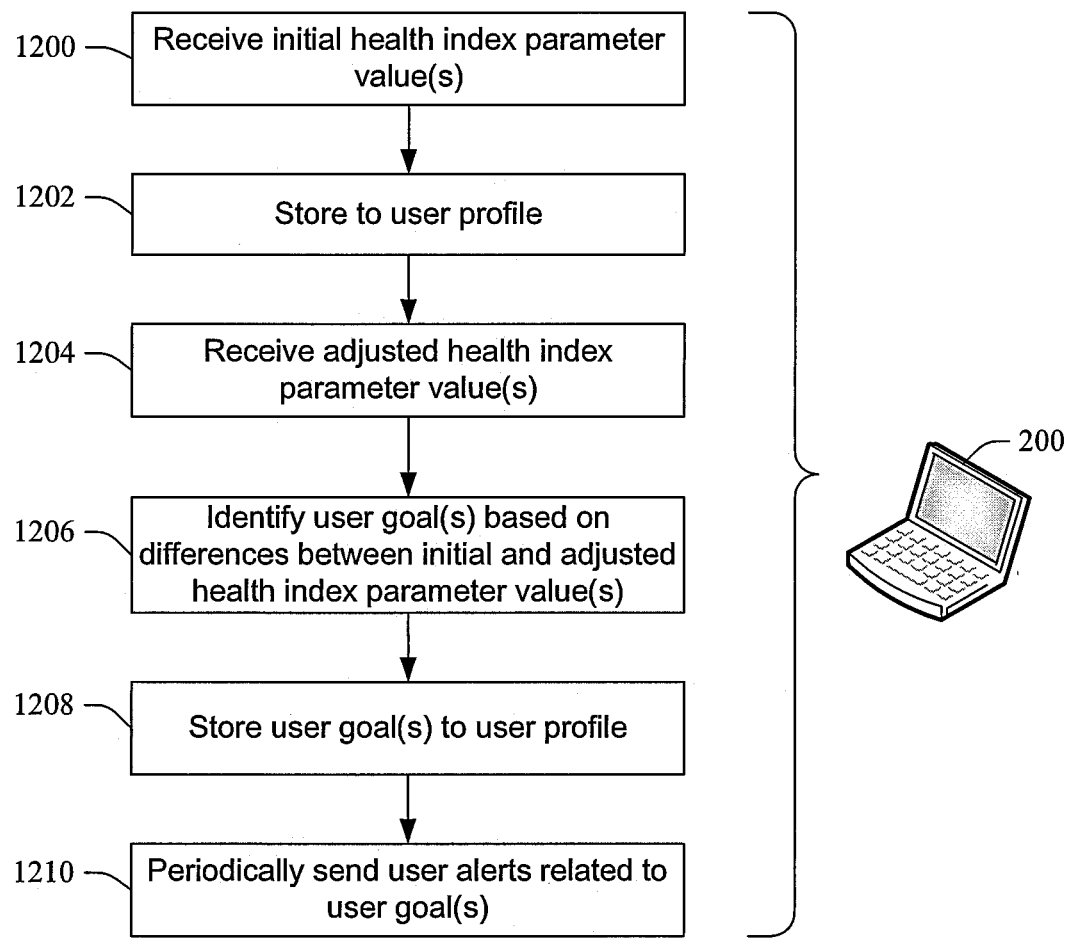
FIG. 12 illustrates a method for providing alerts and/or health-related information to a user who has used the health index calculator to set health behavior goals in accordance with one or more aspects described herein.

FIG. 12 illustrates a method for providing alerts and/or health-related information to a user who has used the health index calculator to set health behavior goals in accordance with one or more aspects described herein. The method may be implemented on one or more computers, such as the computer 200 (FIG. 2) and/or the server and related components of FIG. 1.

At 1200, initial health index parameter values are received. For example, such values may be input by the user into the health index calculator. The received health index parameter values are stored to a user profile for the user, at 1202. At 1204, adjusted health index parameter values are received. For example, the user may adjust the slider bars 705 (FIG. 7) to adjust the values of one or more health index parameters from a current value to a target or goal value. At 1206, user goals are identified based on differences between initial and adjusted health index parameter values. At 1208, the user's goals (i.e. target health index parameter values) are stored to the user profile. At 1210, an alert is transmitted to the user via the user's device (e.g. computer, smartphone, tablet, etc.), wherein the alert includes a reminder to the user to take action toward achieving users health related roles. The alert may be in the form of an email (e.g., including images and/or subject line), a text or SMS message, an MMS message, a "tweet," a message on a social media website or application, or any other suitable means for communicating the subject information to the user. Additionally, the alert may include one or more links to additional information related to the health index parameter value the user is attempting to improve and/or to one or more products related to improvement of the health index parameter value. In this manner, the method of FIG. 12 facilitates providing useful content to a user wherein the provided content is tailored to user specified health improvement goals.

Figure 13:
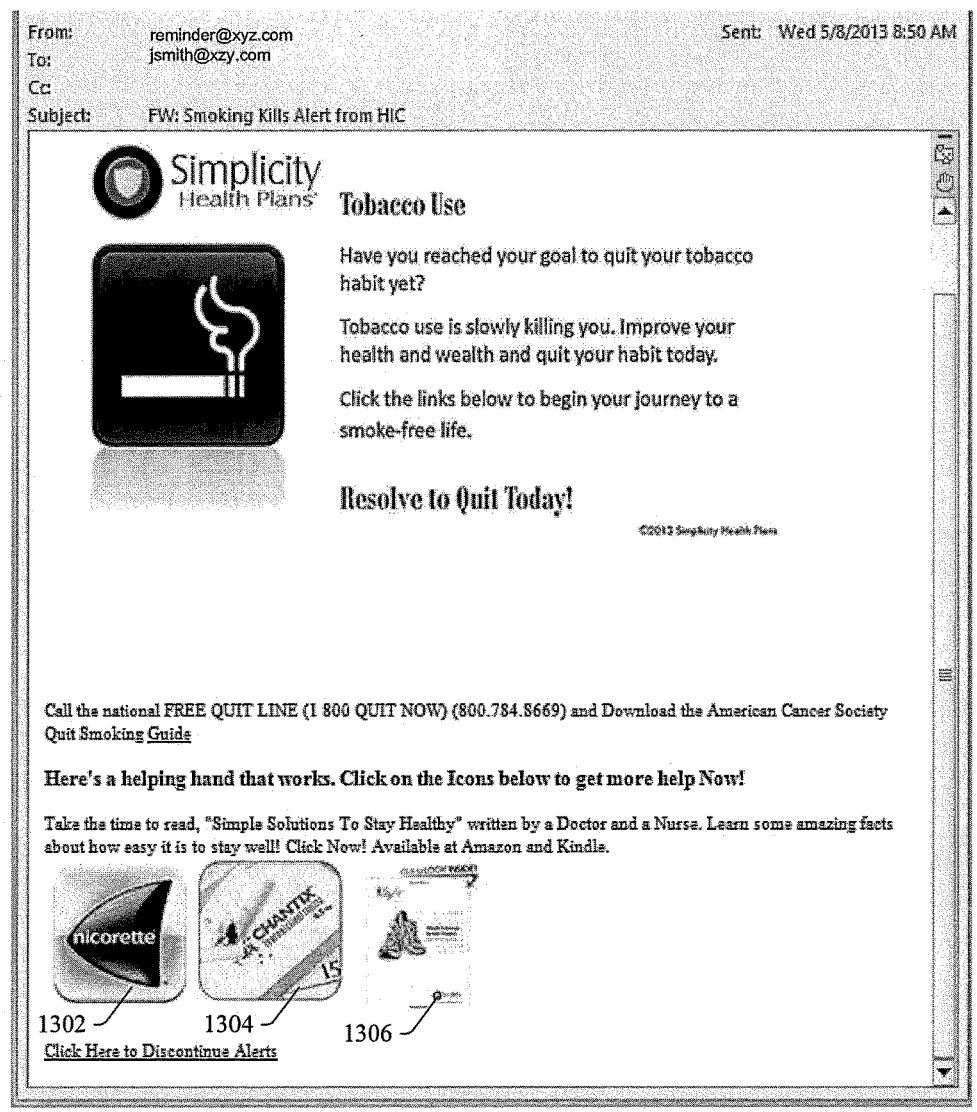
FIG. 13 shows a screenshot of an alert such as can be sent to the user via e-mail, text, etc., in accordance with one or more aspects described herein.

FIG. 13 shows a screenshot of an alert 1300 such as can be sent to the user via e-mail, text, or any other suitable means, in accordance with one or more aspects described herein. In the example of FIG. 13, the user has received an e-mail with a message encouraging the user to stop smoking. Also presented in the e-mail, in addition to message, are icons 1302, 1304 representing links to third-party vendors' sites for products relating to smoking cessation, and an icon 1306 that represents a link to third-party vendor site for product (e.g., a book) for improving personal health. It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A system that facilitates calculating a monetary cost associated with an individual's health index, comprising:
   a processor that executes computer-executable instructions for calculating a user's health index and a monetary cost associated therewith;
   a computer-readable medium that stores the computer-executable instructions; and
   a server comprising the processor and the computer-readable medium and configured to provide Internet access to the processor for presenting calculated cost information to the user via a graphical user interface on a user device;
   wherein the instructions comprise:
      receiving a plurality of individual health index parameter values, the health index parameter values including values related to biometric data associated with the user and health behavior data associated with the user;
      calculating a cost of each health index parameter;
      aggregating the costs of each health index parameter;
      providing the costs of each health index parameter and the aggregate cost to the user;
      receiving input related to an adjustment to at least one health index parameter value;
      updating the costs of each adjusted health index parameter and updating the aggregate cost; and
      providing the updated cost of each health index parameter and the updated aggregate cost to the user in real time;
      calculating a difference between the aggregate cost and the recalculated aggregate cost, the difference representing a dollar amount saved by the user over a predetermined time period as a result of the at least one adjusted health index parameter;
      calculating a return on investment value from the calculated difference, a user-specified investment frequency and annual interest rate;
      calculating a tax savings value from the calculated difference, the return on investment value, and a user-specified tax rate; and
      providing the calculated difference, return on investment value, and tax savings value to the user device;
      calculating one or more of an estimated number of work days missed and a lost-productivity dollar amount from the health index parameter values;
      wherein the health index parameter values are specific to the user and comprise one or more individual values associated with the biometric data, wherein the biometric data comprises one or more of body mass index, cholesterol level, glucose level, and blood pressure;
      and wherein the cost associated with each given individual health index parameter is calculated based on one or more user-adjustable cost values retrieved from a lookup table for the given individual health index parameter value, which is specific to the user and includes the biometric data, prior to aggregation.

2. The system according to claim 1, the instructions further comprising:
   providing to the user an itemized list of the cost of each health index parameter.

3. The system according to claim 1, wherein the biometric data comprises one or more of:
   diastolic blood pressure information;
   blood glucose level information;
   body weight information; and
   total cholesterol level information.

4. The system according to claim 1, wherein the health behavior data comprises one or more of:
   daily tobacco use information;
   daily alcohol intake information;
   stress level information; and
   physical activity level information.

5. The system according to claim 1, the instructions further comprising:
   generating and storing a user profile that comprises user entered health parameter values.

6. The system according to claim 5, the instructions further comprising:
   receiving information related to at least one user specified health behavior goal; and
   storing the at least one user specified health behavior goal to the user profile.

7. The system according to claim 6, the instructions further comprising:
   transmitting to the user device an alert that reminds the user to take action to achieve the user specified health behavior goal.

8. A method of calculating a monetary cost associated with an individual's health index, comprising:
   receiving a plurality of individual health index parameter values, the health index parameter values including values related to biometric data associated with the user and health behavior data associated with the user;
   calculating a cost of each health index parameter;
   aggregating the costs of each health index parameter;
   providing the costs of each health index parameter and the aggregate cost to the user;
   receiving input related to an adjustment to at least one health index parameter value;
   updating the costs of each adjusted health index parameter and updating the aggregate cost; and
   providing the updated cost of each health index parameter and the updated aggregate cost to the user in real time;
   calculating a difference between the aggregate cost and the recalculated aggregate cost, the difference representing a dollar amount saved by the user over a predetermined time period as a result of the at least one adjusted health index parameter;
   calculating a return on investment value from the calculated difference, a user-specified investment frequency and annual interest rate;
   calculating a tax savings value from the calculated difference, the return on investment value, and a user-specified tax rate; and
   providing the calculated difference, return on investment value, and tax savings value to the user device;
   calculating one or more of an estimated number of work days missed and a lost-productivity dollar amount from the health index parameter values;
   wherein the health index parameter values are specific to the user and comprise one or more individual values associated with the biometric data, wherein the biometric data comprises one or more of body mass index, cholesterol level, glucose level, and blood pressure;

and wherein the cost associated with each given individual health index parameter is calculated based on one or more user-adjustable cost values retrieved from a lookup table for the given individual health index parameter value, which is specific to the user and includes the biometric data, prior to aggregation.

9. The method according to claim 8, further comprising: providing to the user an itemized list of the cost of each health index parameter.

10. The method according to claim 8, wherein the biometric data comprises one or more of:
   diastolic blood pressure information;
   blood glucose level information;
   body weight information; and
   total cholesterol level information; and
   wherein the health behavior data comprises one or more of:
   daily tobacco use information;
   daily alcohol intake information;
   stress level information; and
   physical activity level information.

11. The method according to claim 8, further comprising:
   generating and storing a user profile that comprises user entered health parameter values;
   receiving information related to at least one user specified health behavior goal;
   storing the at least one user specified health behavior goal to the user profile; and
   transmitting to the user device an alert that reminds the user to take action to achieve the user specified health behavior goal.

12. The method according to claim 11, wherein the alert is transmitted to the user device at a predetermined time of day in order to encourage the user to behave in a manner that facilitates achieving the user specified health behavior goal.

* * * * *